US005759790A

United States Patent [19]

Lerman et al.

[11] Patent Number: 5,759,790
[45] Date of Patent: Jun. 2, 1998

[54] VON HIPPEL - LINDAU (VHL) DISEASE GENE AND CORRESPONDING CDNA AND METHODS FOR DETECTING CARRIERS OF THE VHL DISEASE GENE

[75] Inventors: Michael I. Lerman, Rockville; Farida Latif, Frederick; Berton Zbar, Garrett Park; Marston Linehan, Rockville, all of Md.

[73] Assignee: The United States of America as represented by the Department of Health and Human Services, Washington, D.C.

[21] Appl. No.: 462,611

[22] Filed: Jun. 5, 1995

Related U.S. Application Data

[62] Division of Ser. No. 61,889, May 14, 1993, Pat. No. 5,654,138.

[51] Int. Cl.$^6$ .................... G01N 33/574; G01N 33/53; A61K 38/00; C07K 5/00
[52] U.S. Cl. .................... 435/7.23; 435/7.1; 436/63; 436/64; 530/324; 530/350; 530/387.7; 530/388.8
[58] Field of Search ...................... 435/7.23, 7.1; 436/63, 64; 530/350, 324, 387.7, 388.1, 388.15, 388.8

[56] References Cited

PUBLICATIONS

Seizinger, B.R., et al. (1991), *Proc. Natl. Acad. Sci. USA*, 88: 2864–2868.
Vance, J.M., et al. (1992) *Am J. Hum. Genet.*, 51 (suppl.) A203, Abstract 800.
Glenn G.M., et al. (1992), *JAMA*, 1226–1231.
Latif, F., et al. (1993), *Cancer Res.*, 63: 861–867.
Crossey, P.A. et al. (Mar. 1993) *Human Mol. Genetics*, 2:279–282.
Lerman, M.I. et al. (1992), *Am J. Hum. Genet.*, 51 (suppl.) A63, Abstract 241.
Tory, K., et al. (1992), *Genomics*, 13: 275–286.
Seizinger, B.R., et al. (1988), *Nature*, 332: 268–269.
Richards, F.M., et al. (1993), *J. Med. Genet.*, 30: 104–107.
Hosoe, S., et al. (1990) *Genomics*, 8: 634–640.
Maher, E.R., et al. (1990), *Genomics*, 10: 957–960.
Glenn, G.M., et al. (1990), *Hum. Genet.*, 87: 207–210.
Latif, F., et al. (1992), *Am J. Hum. Genet.*, 51 (suppl.) A63, Abstract 240.

*Primary Examiner*—Lila Feisee
*Assistant Examiner*—Yvonne Eyler
*Attorney, Agent, or Firm*—Morgan & Finnegan, L.L.P.

[57] ABSTRACT

The invention is the Von Hippel-Lindau (VHL) disease gene and its corresponding cDNA protein product, and antibodies therefore. Methods for detecting carriers of the VHL disease gene using probes derived from the cDNAs are described. Antibodies and methods of detecting the Von-Hippel-Lindau protein are also described.

7 Claims, 9 Drawing Sheets

NORMAL

"VA" Patient 5,759,790

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
  ( A ) LENGTH: 1816 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1:

| | | | | |
|---|---|---|---|---|
| CCTCGCCTCC | GTTACAACAG | CCTACGGTGC | TGGAGGATCC | 40 |
| TTCTGCGCAC | GCGCACAGCC | TCCGGCCGGC | TATTTCCGCG | 80 |
| AGCGCGTTCC | ATCCTCTACC | GAGCGCGCGC | GAAGACTACG | 120 |
| GAGGTCGACT | CGGGAGCGCG | CACGCAGCTC | CGCCCCGCGT | 160 |
| CCGACCCGCG | GATCCCGCGG | CGTCCGGCCC | GGGTGGTCTG | 200 |
| GATCGCGGAG | GGAATGCCCC | GGAGGGCGGA | GAACTGGGAC | 240 |
| GAGGCCGAGG | TAGGCGCGGA | GGAGGCAGGC | GTCGAAGAGT | 280 |
| ACGGCCCTGA | AGAAGACGGC | GGGGAGGAGT | CGGGCGCCGA | 320 |
| GGAGTCCGGC | CCGGAAGAGT | CCGGCCCGGA | GGAACTGGGC | 360 |
| GCCGAGGAGG | AGATGGAGGC | CGGGCGGCCG | CGGCCCGTGC | 400 |
| TGCGCTCGGT | GAACTCGCGC | GAGCCCTCCC | AGGTCATCTT | 440 |
| CTGCAATCGC | AGTCCGCGCG | TCGTGCTGCC | CGTATGGCTC | 480 |
| AACTTCGACG | GCGAGCCGCA | GCCCTACCCA | ACGCTGCCGC | 520 |
| CTGGCACGGG | CCGCCGCATC | CACAGCTACC | GAGGTCACCT | 560 |
| TTGGCTCTTC | AGAGATGCAG | GGACACACGA | TGGGCTTCTG | 600 |
| GTTAACCAAA | CTGAATTATT | TGTGCCATCT | CTCAATGTTG | 640 |
| ACGGACAGCC | TATTTTTGCC | AATATCACAC | TGCCAGTGTA | 680 |
| TACTCTGAAA | GAGCGATGCC | TCCAGGTTGT | CCGGAGCCTA | 720 |
| GTCAAGCCTG | AGAATTACAG | GAGACTGGAC | ATCGTCAGGT | 760 |
| CGCTCTACGA | AGATCTGGAA | GACCACCCAA | ATGTGCAGAA | 800 |
| AGACCTGGAG | CGGCTGACAC | AGGAGCGCAT | TGCACATCAA | 840 |
| CGGATGGGAG | ATTGAAGATT | TCTGTTGAAA | CTTACACTGT | 880 |
| TTCATCTCAG | CTTTTGATGG | TACTGATGAG | TCTTGATCTA | 920 |
| GATACAGGAC | TGGTTCCTTC | CTTAGTTTCA | AAGTGTCTCA | 960 |
| TTCTCAGAGT | AAAATAGGCA | CCATTGCTTA | AAAGAAAGTT | 1000 |
| AACTGACTTC | ACTAGGCATT | GTGATGTTTA | GGGGCAAACA | 1040 |
| TCACAAAATG | TAATTTAATG | CCTGCCCATT | AGAGAAGTAT | 1080 |
| TTATCAGGAG | AAGGTGGTGG | CATTTTGCT | TCCTAGTAAG | 1120 |
| TCAGGACAGC | TTGTATGTAA | GGAGGTTTAT | ATAAGTAATT | 1160 |
| CAGTGGGAAT | TGCAGCATAT | CGTTTAATTT | TAAGAAGGCA | 1200 |
| TTGGCATCTG | CTTTTAATGG | ATGTATAATA | CATCCATTCT | 1240 |
| ACATCCGTAG | CGGTTGGTGA | CTTGTCTGCC | TCCTGCTTTG | 1280 |
| GGAAGACTGA | GGCATCCGTG | AGGCAGGGAC | AAGTCTTTCT | 1320 |
| CCTCTTTGAG | ACCCCAGTGC | CTGCACATCA | TGAGCCTTCA | 1360 |
| GTCAGGGTTT | CTCAGAGGAA | CAAACCAGGG | GACACTTTGT | 1400 |
| TAGAAAGTGC | TTAGAGGTTC | TGCCTCTATT | TTTGTTGGGG | 1440 |

| | | | |
|---|---|---|---|
| GGTGGGAGAG | GGGACCTTAA | AATGTGTACA | GTGAACAAAT | 1480 |
| GTCTTAAAGG | GAATCATTTT | TGTAGGAAGC | ATTTTTTATA | 1520 |
| ATTTTCTAAG | TCGTGCACTT | TCTCGGTCCA | CTCTTGTTGA | 1560 |
| AGTGCTGTTT | TATTACTGTT | TCTAAACTAG | GATTGACATT | 1600 |
| CTACAGTTGT | GATAATAGCA | TTTTGTAAC | TTGCCATCCG | 1640 |
| CACAGAAAAT | ACGAGAAAAT | CTGCATGTTT | GATTATAGTA | 1680 |
| TTAATGGACA | AATAAGTTTT | TGCTAAATGT | GAGTATTTCT | 1720 |
| GTTCCTTTTT | GTAAATATGT | GACATTCCTG | ATTGATTTGG | 1760 |
| GTTTTTTTGT | TGTTGTTGTT | TTGTTTTGTT | TTGTTTTTTT | 1800 |
| GGGATGGAGG | GAATTC | | | 1816 |

( 2 ) INFORMATION FOR SEQ ID NO:2:

( i ) SEQUENCE CHARACTERISTICS:
        ( A ) LENGTH: 284 amino acid residues
        ( B ) TYPE: amino acid
        ( C ) STRANDEDNESS: unknown
        ( D ) TOPOLOGY: unknown ( x i ) SEQUENCE DESCRIPTION: SEQ ID NO:2:

```
Pro  Arg  Leu  Arg  Tyr  Asn  Ser  Leu  Arg  Cys  Trp  Arg  Ile  Leu  Leu
                    5                   10                       15

Arg  Thr  Arg  Thr  Ala  Ser  Gly  Arg  Leu  Phe  Pro  Arg  Ala  Arg  Ser
                    20                  25                       30

Ile  Leu  Tyr  Arg  Ala  Arg  Ala  Lys  Thr  Thr  Glu  Val  Asp  Ser  Gly
                    35                  40                       45

Ala  Arg  Thr  Gln  Leu  Arg  Pro  Ala  Ser  Asp  Pro  Arg  Ile  Pro  Arg
                    50                  55                       60

Arg  Pro  Ala  Arg  Val  Val  Trp  Ile  Ala  Glu  Gly  Met  Pro  Arg  Arg
                    65                  70                       75

Ala  Glu  Asn  Trp  Asp  Glu  Ala  Glu  Val  Gly  Ala  Glu  Glu  Ala  Gly
                    80                  85                       90

Val  Glu  Glu  Tyr  Gly  Pro  Glu  Glu  Asp  Gly  Gly  Glu  Glu  Ser  Gly
                    95                  100                      105

Ala  Glu  Glu  Ser  Gly  Pro  Glu  Glu  Ser  Gly  Pro  Glu  Glu  Leu  Gly
                    110                 115                      120

Ala  Glu  Glu  Glu  Met  Glu  Ala  Gly  Arg  Pro  Arg  Pro  Val  Leu  Arg
                    125                 130                      135

Ser  Val  Asn  Ser  Arg  Glu  Pro  Ser  Gln  Val  Ile  Phe  Cys  Asn  Arg
                    140                 145                      150

Ser  Pro  Arg  Val  Val  Leu  Pro  Val  Trp  Leu  Asn  Phe  Asp  Gly  Glu
                    155                 160                      165

Pro  Gln  Pro  Tyr  Pro  Thr  Leu  Pro  Pro  Gly  Thr  Gly  Arg  Arg  Ile
                    170                 175                      180

His  Ser  Tyr  Arg  Gly  His  Leu  Trp  Leu  Phe  Arg  Asp  Ala  Gly  Thr
                    185                 190                      195

His  Asp  Gly  Leu  Leu  Val  Asn  Gln  Thr  Glu  Leu  Phe  Val  Pro  Ser
                    200                 205                      210

Leu  Asn  Val  Asp  Gly  Gln  Pro  Ile  Phe  Ala  Asn  Ile  Thr  Leu  Pro
                    215                 220                      225

Val  Tyr  Thr  Leu  Lys  Glu  Arg  Cys  Leu  Gln  Val  Val  Arg  Ser  Leu
                    230                 235                      240

Val  Lys  Pro  Glu  Asn  Tyr  Arg  Arg  Leu  Asp  Ile  Val  Arg  Ser  Leu
```

|     |     |     |     | 245 |     |     |     |     | 250 |     |     |     |     | 255 |
| --- | --- | --- | --- | --- | --- | --- | --- | --- | --- | --- | --- | --- | --- | --- |
| Tyr | Glu | Asp | Leu | Glu | Asp | His | Pro | Asn | Val | Gln | Lys | Asp | Leu | Glu |
|     |     |     |     | 260 |     |     |     |     | 265 |     |     |     |     | 270 |
| Arg | Leu | Thr | Gln | Glu | Arg | Ile | Ala | His | Gln | Arg | Met | Gly | Asp |     |
|     |     |     |     | 275 |     |     |     |     | 280 |     |     |     |     |     |

( 2 ) INFORMATION FOR SEQ ID NO:3:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

ATAGTGGAAA TACAGTAACG AGTTGGCCTA GCCTCGC                                              37

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CCCAGCTGGG TCGGGCCTAA GCGCCGGGCC CGT                                                33

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GTGGCTCTTT AACAACCTTT GCTTGTCCCG ATA                                                33

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CAAGTGGTCT ATCCTGTACT TACCACAACA CCT                                               33

( 2 ) INFORMATION FOR SEQ ID NO:7:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TGTATACTCT GAAAGAGCGA TGCCTCCAGG T                                                   31

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single ( D ) TOPOLOGY: linear ( x i ) SEQUENCE DESCRIPTION: SEQ ID NO:8:

TACCATCAAA AGCTGAGATG AAACAGTGTA AGT 33

( 2 ) INFORMATION FOR SEQ ID NO:9:

( i ) SEQUENCE CHARACTERISTICS:
        ( A ) LENGTH: 14 amino acid residues
        ( B ) TYPE: amino acid
        ( C ) STRANDEDNESS: unknown
        ( D ) TOPOLOGY: unknown ( x i ) SEQUENCE DESCRIPTION: SEQ ID NO:9:

Glu Glu Tyr Gly Pro Glu Glu Asp Gly Gly Glu Glu Ser Gly
                5                    10

( 2 ) INFORMATION FOR SEQ ID NO:10:

( i ) SEQUENCE CHARACTERISTICS:
        ( A ) LENGTH: 13 amino aicd residues
        ( B ) TYPE: amino acid
        ( C ) STRANDEDNESS: unknown
        ( D ) TOPOLOGY: unknown ( x i ) SEQUENCE DESCRIPTION: SEQ ID NO:10:

Gly Thr Gly Arg Arg Ile His Ser Tyr Arg Gly His Leu
              5                   10

( 2 ) INFORMATION FOR SEQ ID NO:11:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CACAAGTGAT GCCTTGTAGC TG 22

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

CAGTAGTGTC CTGTATTTAG TG 22

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GTTGGCTATG GGTAGAATTG G 21

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single ( D ) TOPOLOGY: linear ( x i ) SEQUENCE DESCRIPTION: SEQ ID NO:14:

CAGGGTAGCC TTGATCTAAG T    21

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GGAGGTCCTG AGAATATGTG TCC    23

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

TGTTCAGGCA CACAGTAGAT G    21

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

CATCTTCTGC AATCGCAGTC CGCGCGT    27

( 2 ) INFORMATION FOR SEQ ID NO:18:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

CAAAAGCTGA GATGAAACAG TGTAAGT    27

( 2 ) INFORMATION FOR SEQ ID NO:19:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GTTTGGTTAA CCAGAAGCCC ATCGT    25

( 2 ) INFORMATION FOR SEQ ID NO:20:

( i ) SEQUENCE CHARACTERISTICS:
        ( A ) LENGTH: 24 base pairs
        ( B ) TYPE: nucleic acid

```
      ( C ) STRANDEDNESS: single
      ( D ) TOPOLOGY: linear ( x i ) SEQUENCE DESCRIPTION: SEQ ID NO:20:

GATGGGCTTC TGGTTAACCA AACT                                           24
```

1

VON HIPPEL - LINDAU (VHL) DISEASE GENE AND CORRESPONDING CDNA AND METHODS FOR DETECTING CARRIERS OF THE VHL DISEASE GENE

This is a divisional of application Ser. No. 08/061,889 filed May 14, 1993 now U.S. Pat. No. 5,654,138.

FIELD OF INVENTION

The invention is in the field of tumor suppressor genes. More specifically, the invention relates to the Von Hippel-Lindau (VHL) disease gene and its corresponding cDNA and to methods for detecting carriers of the VHL disease gene using probes derived from the cDNA.

BACKGROUND OF INVENTION

Von Hippel-Lindau (VHL) disease is a familial cancer syndrome. This disease in an autosomal dominant disorder and patients who are heterozygous for mutations in the VHL disease gene are predisposed to a variety of cancers, the most frequent being hemangioblastomas of the central nervous system and retina, renal cell carcinoma (RCC) and pheochromocytoma. The multisystem character of the illness, combined with the fact multiple tumors may form in each target organ, produces considerable morbidity and mortality as evidenced by the reduction in life expectancy of affected individuals to 49 years (McKusick, V. A., Mendelian Inheritance in Man (1983) Johns Hopkins University Press, Baltimore and London, p 534–535). Although the prevalence of VHL disease is only 1 in 36,000, because of its late onset most individuals have children before they realize they have inherited VHL disease. For many years, the only method of presymptomatic or prenatal diagnosis of the disease has been periodic examination of the eye, brain, and abdomen in all asymptomatic members of VHL families. Unfortunately, examination of all target organs is required to ensure detection of disease that may be limited to a single organ. In addition to the obvious inconvenience and the cost of these examinations, they have the additional drawback that they may not yield definitive diagnostic information. Therefore, in order to develop a method which allows the unequivocal diagnosis of VHL disease in individuals at risk, researchers have focused intensive efforts on identifying and isolating the VHL disease gene.

Results of this research have shown that the VHL, disease gene is a member of the family of tumor suppressor genes (Tory, K. et al. J. Natl. Canc. Inst. (1989) 81:1097–1101; Maher, E. R. et al. J. Med. Genet. (1990) 27:311–314) and that it behaves in accordance with Knudson's theory of human carcinogenesis (Knudson, A., Proc. Natl. Acad Sci. USA (1971) 68:816–823). In addition, the identification of DNA markers tightly linked to the VHL disease gene has allowed localization of the VHL disease gene to human chromosome 3p25–p26. (Hosoe, S. et al. Genomics (1990) 8:634–640; Maher, E. R. et al. Genomics (1990) 8:957–960; Glenn, G. M. et al. Hum. Genet. (1990) 87:207–210, Latif, F. et al. Am J. Hum. Genet. (1992) 51 (suppl.) A63; Tory, K. et al. Genomics (1992) 13:275–286; Richards, F. M. et al. J. Med. Genet. (1993) 30:104–107); Seizinger, B. R. et al. Nature (1988) 332:268–269; Seizinger, B. R. et al. Proc. Natl. Acad. Sci. USA (1991) 88:2864–2868 and Vance J. M. et al. Am J. Hum. Genet. (1993) 51:203–209)). Recently, Glenn et al. (Glenn, G. M. et al. JAMA (1992) 1226–1231) have used DNA markers flanking the VHL disease gene as probes to detect linkage to the VHL disease gene via restriction fragment polymorphism analysis of DNA isolated from individuals who are members of families at risk for VHL disease. Although this DNA polymorphism method results in enhanced accuracy of identification of carriers of VHL disease gene, the method is inherently flawed in that DNA polymorphism analysis does not detect the VHL disease gene itself. More recently, a gene located in the VHL region has been cloned (Latif, F. et al. Cancer Res. (1993) 63:861–867). However, this gene was found to detect no mutations in VHL patients and thus, there are currently no available methods which can identify carriers of the VHL disease gene with 100% accuracy. However, the recent identification and isolation of the VHL disease gene (Latif et al., Science, in press, "Identification of the von Hippel-Lindau Disease Tumor Suppressor Gene") and its corresponding cDNA should allow the development of diagnostic methods which provide unequivocal detection of carriers of the VHL disease gene.

SUMMARY OF INVENTION

The present invention relates to the von Hippel-Lindau (VHL) disease gene and its corresponding cDNA.

The invention further relates to methods for detecting carriers of the VHL disease gene. The first method comprises analyzing DNA of a subject for mutations of the VHL disease gene associated with VHL disease.

The second method comprises analyzing RNA of a subject for mutations or alterations in the VHL-specific mRNA associated with VHL disease.

The third method comprises analyzing protein of a subject for alterations in VHL protein expression associated with VHL disease.

The invention also encompasses recombinant VHL proteins derived from the VHL cDNA and antibodies directed against said VHL proteins or peptides derived therefrom.

The invention further relates to a method for treating a carrier of VHL disease gene in which an expression vector containing a nucleic acid sequence representing wild-type VHL gene is administered to the carrier.

The invention also provides a diagnostic kit for detecting carriers of the VHL disease gene. The kit comprises purified and isolated nucleic acid sequences useful as PCR primers in analyzing DNA or RNA for mutations of the VHL disease gene associated with VHL disease.

BRIEF DESCRIPTION OF THE DRAWINGS

FIG. 2(A) shows low resolution blot containing 2 μg poly A⁺ mRNA, the tissues are indicated above the lanes. FIG. 2(B) shows a high resolution blot containing 1 μg of poly A⁺ mRNA from: lane 1, fetal brain; lane 2, adult brain; lane 3, fetal kidney; lane 4, adult kidney; lane 5, cerebellum;

lane 6, adult adrenal; and lane 7, prostate. The sizes of the transcripts were determined by the position of the 28S and 18S rRNA bands.

Figure 3A:
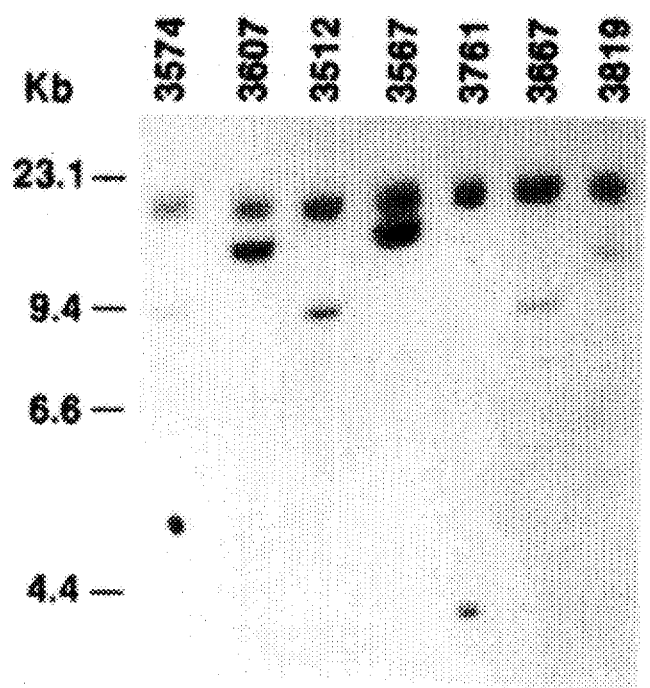
Figure 3B:
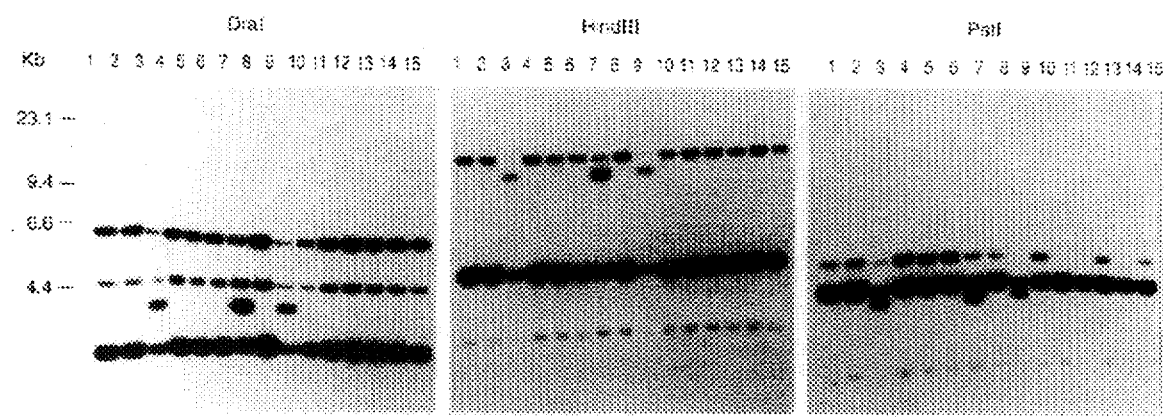
Figure 3C:
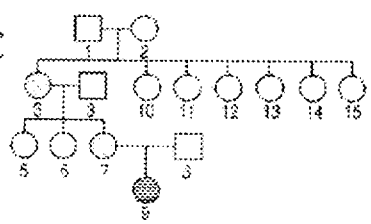
Figure 3D:
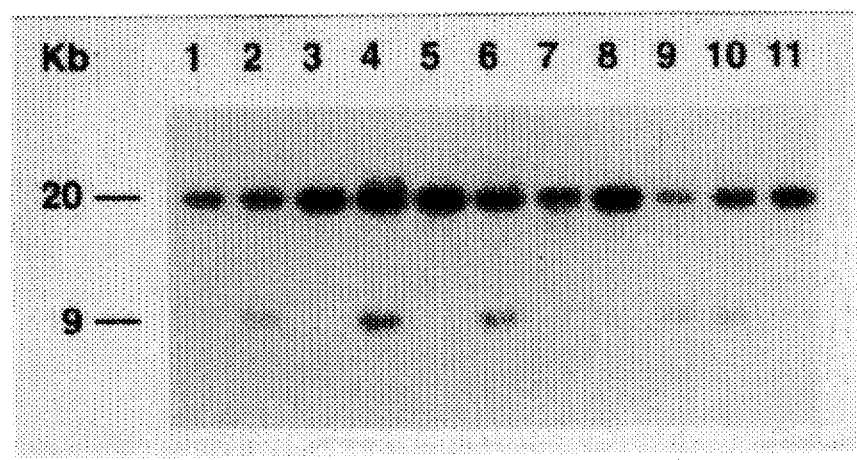
Figure 3E:
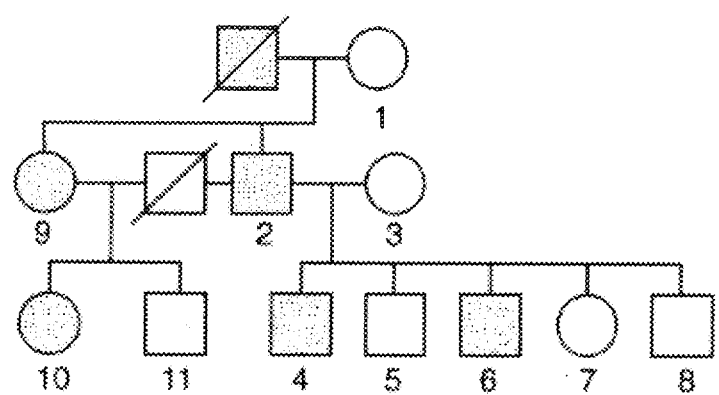

FIGS. 3A–C show detection by Southern blotting analysis of rearrangement mutations in constitutional DNA of VHL affected patients using g7 cDNA as probe. FIG. 3A DNA from lymphoblastoid cell lines of 7 unrelated VHL patients was digested with EcoRI and analyzed by standard blotting procedures. The normal invariant band is about 20 to 22 kb, the sizes of the aberrant bands probably resulting from intragenic deletions range from 4 to 25 kb. The patients code numbers are indicated above the lanes. FIG. 3B DNAs from lymphoblastoid cell lines of pedigree members from a new mutation family (coded "S") digested with DraI, HindIII, and PstI. The pedigree with the position of the affected (filled circles) and predicted (hatched circle) members is shown. Males are represented by squares and females by circles. FIG. 3C Genetic transmission of the mutant allele (the aberrant band) in a regular VHL family (coded "P"). The DNAs were digested with by EcoRI and analyzed by Southern blotting; the pedigree is shown.

FIGS. 4A–C shows Southern blot analysis of genomic DNA of VHL patients (only the initials of each patients name are given). The DNAs were digested with EcoRI and probed using different regions of g7 cDNA. Panel A: Total g7 cDNA probe; Panel B: 5' end probe, nucleotides 3–146; Panel C: 3' end probe nucleotides 1277–1600.

Figure 5A:
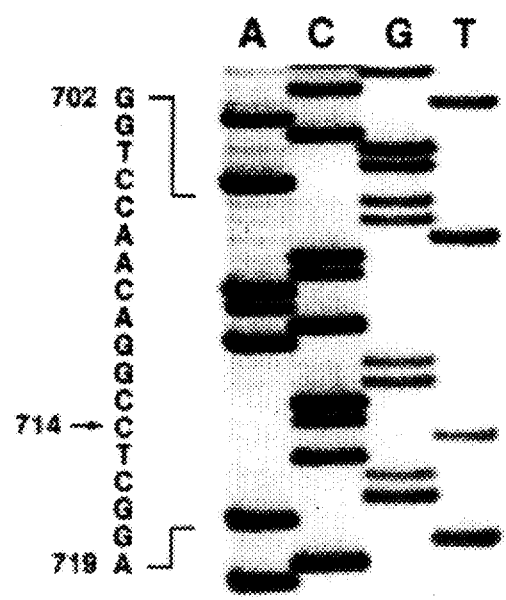
Figure 5B:
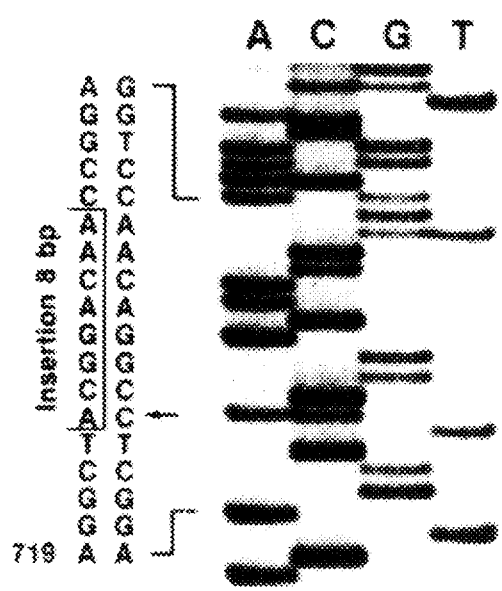

FIG. 5A–B shows the results of polymerase chain reaction-single stranded conformation analysis (PCR-SSCP) of the genomic DNA of VHL patients with the 8 bp insertion mutation (Table 1). Portions of the DNA sequencing gels are shown that display normal and 714insTTGTCCGT mutation sequences. The DNA sequence is of the antisense strand; therefore, the inserted bases are 5'ACGGACAA3'. Adjacent to sequencing ladder are shown the positions of the insertion, and the nature of the insertion, as predicted from the sequence.

Figure 6:
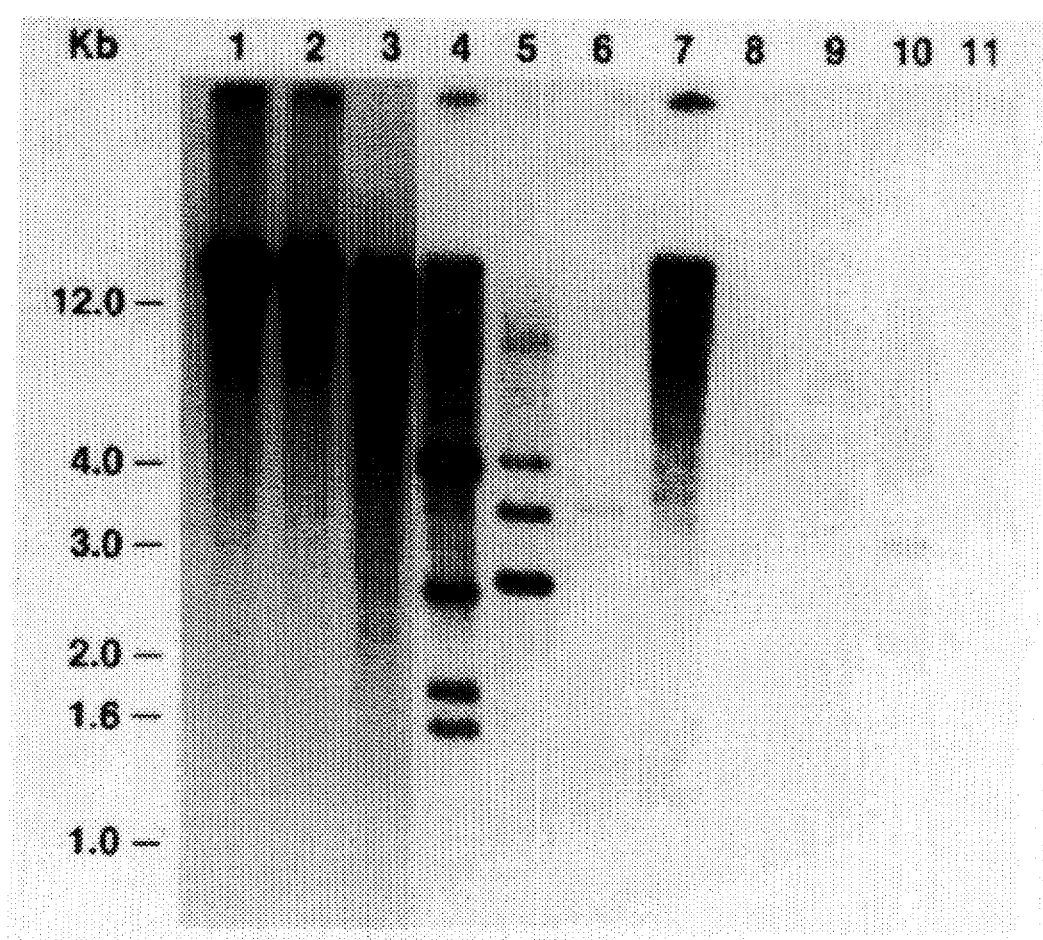

FIG. 6 shows the results of a "zoo" blot illustrating evolutionary conservation of the putative VHL gene. The g7 cDNA shows cross species homology to DNA from mammals, birds, fly, and sea urchin. Lanes: 1, human (Homo sapiens); 2, chimpanzee (Pan troglodytes); 3, macaque (Macaca fascicularis); 4, cow (Bovis domesticus); 5, rat (Rattus norvigicus); 6, mouse (Mus musculus); 7, chicken (Gallus domesticus); 8, frog (Xenopus laevis); 9, fly (Drosophila melanogaster); 10, sea urchin (Strongilocetrotus purpuratus); and 11, yeast (Saccharomyces ceriviseae).

DETAILED DESCRIPTION OF THE INVENTION

The present invention relates to the VHL disease gene and its corresponding cDNA. Recently, the region of human chromosome 3 containing the VHL disease gene has been cloned by genomic walking with yeast artificial chromosomes (YACS) and the cloned DNA recovered with cosmids from a chromosome 3 specific library (Latif et al. Science, in press). The phage 191 which contains the VHL disease gene was deposited with the American Type Culture Collection (ATCC), 12301 Parklawn Drive, Rockville, Md. 20852 on May 13, 1993 and has been granted ATCC Deposit No. 69311. This VHL disease gene represents the wild-type VHL gene where wild-type means the gene not causing VHL disease.

The present invention is also directed to a cDNA corresponding to the VHL disease gene. This cDNA sequence, designated g7, is set forth below as SEQ ID NO: 1 and was deposited with the American Type Culture Collection on May 13, 1993 and has been granted ATCC Deposit No. 69312. This cDNA also has GenBank accession No. L15409.

```
CCTCGCCTCC GTTACAACAG CCTACGGTGC TGGAGGATCC TTCTGCGCAC   50
GCGCACAGCC TCCGGCCGGC TATTTCCGCG AGCGCGTTCC ATCCTCTACC  100
GAGCGCGCGC GAAGACTACG GAGGTCGACT CGGGAGCGCG CACGCAGCTC  150
CGCCCCGCGT CCGACCCGCG GATCCCGCGG CGTCCGGCCC GGGTGGTCTG  200
GATCGCGGAG GGAATGCCCC GGAGGGCGGA GAACTGGGAC GAGGCCGAGG  250
TAGGCGCGGA GGAGGCAGGC GTCGAAGAGT ACGGCCCTGA AGAAGACGGC  300
GGGGAGGAGT CGGGCGCCGA GGAGTCCGGC CCGGAAGAGT CCGGCCCGGA  350
GGAACTGGGC GCCGAGGAGG AGATGGAGGC CGGGCGGCCG CGGCCCGTGC  400
TGCGCTCGGT GAACTCGCGC GAGCCCTCCC AGGTCATCTT CTGCAATCGC  450
AGTCCGCGCG TCGTGCTGCC CGTATGGCTC AACTTCGACG GCGAGCCGCA  500
GCCCTACCCA ACGCTGCCGC CTGGCACGGG CCGCCGCATC CACAGCTACC  550
GAGGTCACCT TTGGCTCTTC AGAGATGCAG GGACACACGA TGGGCTTCTG  600
GTTAACCAAA CTGAATTATT TGTGCCATCT CTCAATGTTG ACGGACAGCC  650
TATTTTTGCC AATATCACAC TGCCAGTGTA TACTCTGAAA GAGCGATGCC  700
TCCAGGTTGT CCGGAGCCTA GTCAAGCCTG AGAATTACAG GAGACTGGAC  750
ATCGTCAGGT CGCTCTACGA AGATCTGGAA GACCACCCAA ATGTGCAGAA  800
AGACCTGGAG CGGCTGACAC AGGAGCGCAT TGCACATCAA CGGATGGGAG  850
ATTGAAGATT TCTGTTGAAA CTTACACTGT TTCATCTCAG CTTTTGATGG  900
TACTGATGAG TCTTGATCTA GATACAGGAC TGGTTCCTTC CTTAGTTTCA  950
```

-continued

```
AAGTGTCTCA TTCTCAGAGT AAAATAGGCA CCATTGCTTA AAAGAAAGTT 1000
AACTGACTTC ACTAGGCATT GTGATGTTTA GGGGCAAACA TCACAAAATG 1050
TAATTTAATG CCTGCCCATT AGAGAAGTAT TTATCAGGAG AAGGTGGTGG 1100
CATTTTTGCT TCCTAGTAAG TCAGGACAGC TTGTATGTAA GGAGGTTTAT 1150
ATAAGTAATT CAGTGGGAAT TGCAGCATAT CGTTTAATTT TAAGAAGGCA 1200
TTGGCATCTG CTTTTAATGG ATGTATAATA CATCCATTCT ACATCCGTAG 1250
CGGTTGGTGA CTTGTCTGCC TCCTGCTTTG GGAAGACTGA GGCATCCGTG 1300
AGGCAGGGAC AAGTCTTTCT CCTCTTTGAG ACCCCAGTGC CTGCACATCA 1350
TGAGCCTTCA GTCAGGGTTT CTCAGAGGAA CAAACCAGGG GACACTTTGT 1400
TAGAAAGTGC TTAGAGGTTC TGCCTCTATT TTTGTTGGGG GGTGGGAGAG 1450
GGGACCTTAA AATGTGTACA GTGAACAAAT GTCTTAAAGG GAATCATTTT 1500
TGTAGGAAGC ATTTTTTATA ATTTTCTAAG TCGTGCACTT TCTCGGTCCA 1550
CTCTTGTTGA AGTGCTGTTT TATTACTGTT TCTAAACTAG GATTGACATT 1600
CTACAGTTGT GATAATAGCA TTTTTGTAAC TTGCCATCCG CACAGAAAAT 1650
ACGAGAAAAT CTGCATGTTT GATTATAGTA TTAATGGACA AATAAGTTTT 1700
TGCTAAATGT GAGTATTTCT GTTCCTTTTT GTAAATATGT GACATTCCTG 1750
ATTGATTTGG GTTTTTTTGT TGTTGTTGTT TTGTTTTGTT TTGTTTTTTT 1800
GGGATGGAGG GAATTC                                      1816
```

The abbreviations used for the nucleotides are those standardly used in the art.

The deduced amino acid sequence of the g7 cDNA is shown as SEQ ID NO:2 below and starts at nucleotide 1 of SEQ ID NO:1 and extends 851 nucleotides.

| Pro | Arg | Leu | Arg | Tyr 5 | Asn | Ser | Leu | Arg | Cys 10 | Trp | Arg | Ile | Leu | Leu 15 |
|---|---|---|---|---|---|---|---|---|---|---|---|---|---|---|
| Arg | Thr | Arg | Thr | Ala 20 | Ser | Gly | Arg | Leu | Phe 25 | Pro | Arg | Ala | Arg | Ser 30 |
| Ile | Leu | Tyr | Arg | Ala 35 | Arg | Ala | Lys | Thr | Thr 40 | Glu | Val | Asp | Ser | Gly 45 |
| Ala | Arg | Thr | Gln | Leu 50 | Arg | Pro | Ala | Ser | Asp 55 | Pro | Arg | Ile | Pro | Arg 60 |
| Arg | Pro | Ala | Arg | Val 65 | Val | Trp | Ile | Ala | Glu 70 | Gly | Met | Pro | Arg | Arg 75 |
| Ala | Glu | Asn | Trp | Asp 80 | Glu | Ala | Glu | Val | Gly 85 | Ala | Glu | Glu | Ala | Gly 90 |
| Val | Glu | Glu | Tyr | Gly 95 | Pro | Glu | Glu | Asp | Gly 100 | Gly | Glu | Glu | Ser | Gly 105 |
| Ala | Glu | Glu | Ser | Gly 110 | Pro | Glu | Glu | Ser | Gly 115 | Pro | Glu | Glu | Leu | Gly 120 |
| Ala | Glu | Glu | Glu | Met 125 | Glu | Ala | Gly | Arg | Pro 130 | Arg | Pro | Val | Leu | Arg 135 |
| Ser | Val | Asn | Ser | Arg 140 | Glu | Pro | Ser | Gln | Val 145 | Ile | Phe | Cys | Asn | Arg 150 |
| Ser | Pro | Arg | Val | Val 155 | Leu | Pro | Val | Trp | Leu 160 | Asn | Phe | Asp | Gly | Glu 165 |
| Pro | Gln | Pro | Tyr | Pro 170 | Thr | Leu | Pro | Pro | Gly 175 | Thr | Gly | Arg | Arg | Ile 180 |
| His | Ser | Tyr | Arg | Gly 185 | His | Leu | Trp | Leu | Phe 190 | Arg | Asp | Ala | Gly | Thr 195 |
| His | Asp | Gly | Leu | Leu 200 | Val | Asn | Gln | Thr | Glu 205 | Leu | Phe | Val | Pro | Ser 210 |
| Leu | Asn | Val | Asp | Gly 215 | Gln | Pro | Ile | Phe | Ala 220 | Asn | Ile | Thr | Leu | Pro 225 |
| Val | Tyr | Thr | Leu | Lys 230 | Glu | Arg | Cys | Leu | Gln 235 | Val | Val | Arg | Ser | Leu 240 |
| Val | Lys | Pro | Glu | Asn 245 | Tyr | Arg | Arg | Leu | Asp 250 | Ile | Val | Arg | Ser | Leu 255 |

| Tyr | Glu | Asp | Leu | Glu 260 | Asp | His | Pro | Asn | Val 265 | Gln | Lys | Asp | Leu | Glu 270 |
|---|---|---|---|---|---|---|---|---|---|---|---|---|---|---|
| Arg | Leu | Thr | Gln | Glu 275 | Arg | Ile | Ala | His | Gln 280 | Arg | Met | Gly | Asp | |

Variations are contemplated in the cDNA sequence shown in SEQ ID NO:1 which will result in a DNA sequence that is capable of directing production of analogs of the VHL protein shown in SEQ ID NO. 2. It should be noted that the DNA sequence set forth above represents a preferred embodiment of the present invention. Due to the degeneracy of the genetic code, it is to be understood that numerous choices of nucleotides may be made that will lead to a DNA sequence capable of directing production of the instant VHL protein or its analogs. As such, DNA sequences which are functionally equivalent to the sequence set forth above or which are functionally equivalent to sequences that would direct production of analogs of the VHL protein produced pursuant to the amino acid sequence set forth above, are intended to be encompassed within the present invention.

The term analog includes any protein or polypeptide having an amino acid residue sequence substantially identical to a sequence specifically shown herein in which one or more amino acid residues have been conservatively substituted with a functionally similar residue and which displays the functional aspects of the VHL protein as described herein. Examples of conservative substitutions include, for example, the substitution of one non-polar (i.e. hydrophobic) residue such as isoleucine, valine, leucine or methionine for another; the substitution of one polar (i.e. hydrophilic) residue for another, such as a substitution between arginine and lysine, between glutamine and asparagine, or between glycine and serine; the substitution of one basic residue such as lysine, arginine or histidine for another; or the substitution of one acidic residue, such as aspartic acid or glutamic acid for another.

The phrase conservative substitution may also include the use of a chemically derivatized residue in place of a non-derivatized residue provided that the resulting protein or polypeptide displays the requisite functional activity.

Chemical derivative refers to a VHL protein or polypeptide having one or more residues chemically derivatized by reaction of a functional side group. Examples of such derivatized molecules include, but are not limited to, those molecules in which free amino groups have been derivatized to form, for example, amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters, or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those proteins or peptides which contain one or more naturally-occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. A VHL protein or polypeptide of the present invention also includes any protein or polypeptide having one or more additions and/or deletions of residues relative to the sequence of a protein or polypeptide whose sequence is shown herein, so long as the requisite activity is maintained.

The present invention also relates to methods for detecting carriers of the VHL disease gene.

It is understood by one skilled in the art that the methods for detection disclosed in the present invention can be used prenatally to screen a fetus or presymptomatically to screen a subject at risk through his/her family history. In addition, these methods can be used to determine the involvement of the VHL disease gene in other human malignancies such as kidney, lung and bladder cancers.

In one embodiment of the invention, the method for detecting carriers of the VHL disease gene comprises analyzing the DNA of a subject for mutations of the VHL disease gene associated with VHL disease.

For purposes of the present invention, subject means a mammal and mutation means inversion, translocation, insertion, deletion or point mutation of the VHL disease gene.

For analysis of the DNA, a biological specimen is obtained from the subject. Examples of biological specimens that can be obtained for use in the present method include, but are not limited to, tissue biopsies, whole blood, urine, feces or other samples normally tested in the diagnosis of disease. Preferred biological specimens are whole blood or urine.

Although it is not always required, it is preferable to at least partially purify DNA from the biological specimen prior to analysis. For example, after disruption of cells in the specimen, nucleic acid can be extracted from contaminating cell debris and other protein substances by extraction of the sample with phenol. In phenol extraction, the aqueous sample is mixed with an approximately equal volume of redistilled phenol and centrifuged to separate the two phases. The aqueous phase containing the nucleic acid is removed and precipitated with ethanol to yield nucleic acid free of phenol. Alternatively, DNA can be purified from the biological sample according to Sidransky, D. et al. (Science (1992) 256:102–105; Science (1991) 252:706) or by the method of Glenn et al. (Glenn, G. M. et al. JAMA (1992) 267:1226–1231). The DNA to be analyzed can be either single- or double-stranded.

Methods for analyzing the DNA for mutations in the VHL disease gene include Southern blotting after digestion with the appropriate restriction enzymes (restriction fragment length polymorphism, RFLP) (Botstein, D. Amer. J. Hum. Genet. (1980) 69:201–205), denaturing gradient electrophoresis technique (Myers, R. M., Nature (1985) 313:495–498), oligonucleotide hybridization (Conner, R. et al., EMBO J. (1984) 3:13321–1326), RNase digestion of a duplex between a probe RNA and the target DNA (Winter, E. et al., Proc. Natl. Acad. Sci. U.S.A. (1985) 82:7575–7579), polymerase chain reaction (PCR) (Saiki, P. K. et al., Science (1988) 239:487–491; U.S. Pat. Nos. 4,683,195 and 4,683,202), ligase chain reaction (LCR) (European Patent Application Nos. 0,320,308 and 0,439,182), and PCR-single stranded conformation analysis (PCR-SSCP) (Orita, M. et al., Genomics (1989) 5:874–879; Dean, M. et al. Cell (1990) 61:863–871). In one preferred embodiment, DNA is analyzed by Southern analysis.

The DNA to be analyzed via Southern analysis is digested with one or more restriction enzymes. The restriction enzymes to be used in the present invention are those enzymes for whom the presence or absence of their recognition site is linked to VHL disease. Preferred restriction enzyme include EcoRI, HindIII, PstI, DraI, BamHI, BglI, BglII, and PvuII. Following restriction digestion, resultant DNA fragments are separated by gel electrophoresis and the fragments are detected by hybridization with a labelled nucleic acid probe (Southern, E. M. J. Mol. Biol. (1975) 98:503–517).

The nucleic acid sequence used as a probe in Southern analysis can be labeled in single-stranded or double-stranded form. Labelling of the nucleic acid sequence can be carried out by techniques known to one skilled in the art. Such labelling techniques can include radiolabels and enzymes (Sambrook, J. et al. (1989) in "Molecular Cloning, A Laboratory Manual", Cold Spring Harbor Press, Plainview, N.Y.). In addition, there are known non-radioactive techniques for signal amplification including methods for attaching chemical moieties to pyrimidine and purine rings (Dale, R. N. K. et al. (1973) Proc. Natl. Acad. Sci., 70:2238–2242; Heck, R. F. 1968) S. Am. Chem. Soc., 90:5518–5523), methods which allow detection by chemiluminescence (Barton, S. K. et al. (1992) J. Am. Chem. Soc., 114:8736–8740) and methods utilizing biotinylated nucleic acid probes (Johnson, T. K. et al. (1983) Anal. Biochem., 133:126–131; Erickson, P. F. et al. (1982) J. of Immunology Methods, 51:241–249; Matthaei, F. S. et al. (1986) Anal. Biochem., 157:123–128) and methods which allow detection by fluorescence using commercially available products. The size of the probe can range from about 200 nucleotides to about several kilobases. A preferred probe size is about 500 to about 2000 nucleotides. Each of the nucleic acid sequences used as a probe in Southern analysis is substantially homologous to the corresponding portion of the cDNA sequence shown in SEQ ID NO:1. By "substantially homologous" is meant a level of homology between the nucleic acid sequence used as a probe and the corresponding sequence shown in SEQ ID NO:1. Preferably, the level of homology is in excess of 70%, most preferably in excess of 80%, with a particularly preferred nucleic acid sequence being in excess of 90% homologous with the sequence shown in SEQ ID NO:1. Once the separated DNA fragments are hybridized to the labelled nucleic acid probes, the restriction digest pattern can be visualized by autoradiography and examined for the presence or absence of a restriction fragment length polymorphism (RFLP) associated with VHL disease.

In a second preferred embodiment, the DNA is analyzed for mutations in the VHL disease gene by PCR-SSCP (Orita et al., (1989), Dean et al., (1990)) In this method, each of the pairs of primers selected for use in PCR are designed to hybridize with sequences in the VHL disease gene which are an appropriate distance apart (at least about 50 nucleotides) in the gene to permit amplification and subsequent detection of mutations in the amplification product. Primer pairs which can specifically hybridize to such VHL gene sequences can be derived from the VHL disease gene sequence. In a preferred embodiment, the primers are derived from the cDNA sequence shown in SEQ ID NO.1. Each primer of a pair is a single-stranded oligonucleotide of about 15 to about 50 bases in length which is complementary to a sequence at the 3' end of one of the strands of a double-stranded target sequence. Each pair comprises two such primers, one of which is complementary 3' end and the other of which is complementary to the other 3' end of the target sequence. The target sequence is generally about 100 to about 300 base pairs long but can be as large as 500–600 base pairs. Optimization of the amplification reaction to obtain sufficiently specific hybridization to the VHL disease gene is well within the skill in the art and is preferably achieved by adjusting the annealing temperature.

The present invention also provides purified and isolated pairs of primers for use in analysis of DNA for mutations in the VHL gene. The nucleic acid sequences of these primers is set forth below as SEQ ID NOs:3–8.

SEQ. ID. NO. 3
ATAGTGGAAA TACAGTAACG AGTTGGCCTA GCCTCGC
SEQ. ID. NO. 4
CCCAGCTGGG TCGGGCCTAA GCGCCGGGCC CGT
SEQ. ID. NO. 5
GTGGCTCTTT AACAACCTTT GCTTGTCCCG ATA
SEQ. ID. NO. 6
CAAGTGGTCT ATCCTGTACT TACCACAACA CCT
SEQ. ID. NO. 7
TGTATACTCT GAAAGAGCGA TGCCTCCAGG T
SEQ. ID. NO. 8
TACCATCAAA AGCTGAGATG AAACAGTGTA AGT where SEQ ID NO. 3 and SEQ ID NO. 4 represent one pair of primers; SEQ ID NO. 5 and SEQ ID NO. 6 represent a second pair of primers and SEQ ID NO. 7 and SEQ ID NO. 8 represent a third pair of primers.

The primers of this invention can be synthesized using any of the known methods of oligonucleotide synthesis (e.g., the phosphodiester method of Agarwal et al. 1972. Agnew. Chem. Int. Ed. Engl. 11:451, the phosphotriester method of Hsiung et al. 1979. Nucleic Acids Res. 6:1371, or the automated diethylphosphoramidite method of Beuacage et al. 1981. Tetrahedron Letters 22:1859–1862), or they can be isolated fragments of naturally occurring or cloned DNA. In addition, those skilled in the art would be aware that oligonucleotides can be synthesized by automated instruments sold by a variety of manufacturers or can be commercially custom ordered and prepared. In one embodiment, the primers can be derivatized to include a detectable label suitable for detecting and/or identifying the primer extension products (e.g., biotin, avidin, or radiolabeled dNTP's), or with a substance which aids in the isolation of the products of amplification (e.g. biotin or avidin). In a preferred embodiment, SEQ. ID. NO. 3 through SEQ. ID. NO. 8 are synthetic oligonucleotides.

In an alternative embodiment, primer pairs can be selected to hybridize to mutant forms of the VHL disease gene. The selected primer pairs will hybridize sufficiently specifically to the mutated gene sequences such that non-specific hybridization to wild-type VHL gene sequences will not prevent identification of the amplification product of the mutant gene sequence. Primer pairs which hybridize to mutations in the VHL gene sequence can be used to amplify specific mutant gene sequences present in the DNA of a biological sample.

The amplification products of PCR can be detected either directly or indirectly. In the PCR-SSCP method, direct detection of the amplification products is carried out via labelling of primer pairs. Labels suitable for labelling the primers of the present invention are known to one skilled in the art and include radioactive labels, biotin, avidin, enzymes and fluorescent molecules. The derived labels can be incorporated into the primers prior to performing the amplification reaction. A preferred labelling procedure utilizes radiolabeled ATP and T4 polynucleotide kinase (Sambrook, J. et al. (1989) in "Molecular Cloning, A Laboratory Manual", Cold Spring Harbor Press, Plainview, N.Y.). Alternatively, the desired label can be incorporated into the primer extension products during the amplification reaction in the form of one or more labelled dNTPs. In the present invention, the labelled amplified PCR products can be analyzed for mutations of the VHL gene associated with VHL disease gene via separating the PCR products by denaturing polyacrylamide gel electrophoresis or via direct sequencing of the PCR-products.

In yet another embodiment, unlabelled amplification products can be analyzed for mutations in the VHL disease gene via hybridization with nucleic acid probes radioactively labelled or, labelled with biotin, in Southern blots or dot blots. Nucleic acid probes useful in the embodiment are those described earlier for Southern analysis.

In a second embodiment, the method for detecting carriers of the VHL disease gene comprises analyzing the RNA of a subject for mutations or alterations in VHL-specific mRNA associated with VHL disease.

For the analysis of RNA by this method, RNA derived from blood or a tumor biopsy sample is obtained from said subject where said tumors include, but are not limited to, tumors of the eye brain, liver, kidney, pancreas, and pheochromocytomas.

The RNA to be analyzed can be isolated from blood or tumor biopsy samples as whole cell RNA or as poly(A)$^+$ RNA. Whole cell RNA can be isolated by methods known to those skilled in the art. Such methods include extraction of RNA by differential precipitation (Birnbiom, H. C. (1988) Nucleic Acids Res., 16:1487–1497), extraction of RNa by organic solvents (Chomczynski, P. et al. (1987) Anal. Biochem., 162:156–159) and extraction of RNA with strong denaturants (Chirgwin, J. M. et al. (1979) Biochemistry, 18:5294–5299). Poly(A)$^+$ RNA can be selected from whole cell RNA by affinity chromatography on oligo-d(T) columns (Aviv, H. et al. (1972) Proc. Natl. Acad. Sci. 69:1408–1412). A preferred method of isolating RNA is extraction of whole cell RNA by acid-phenol (Chomczynski et al. 1987).

The methods for analyzing the RNA for alterations in the pattern or level of VHL specific mRNA expression linked to VHL disease include Northern blotting (Alwine, J. C. et al. (1977) Proc. Natl. Acad. Sci., 74:5350–5354), dot and slot hybridization (Kafatos, F. C. et al. (1979) Nucleic Acids Res., 7:1541–1522), filter hybridization (Hollander, M. C. et al. (1990) Biotechniques; 9:174–179), RNase protection (Sambrook, J. et al. (1989) in "Molecular Cloning, A Laboratory Manual", Cold Spring Harbor Press, Plainview, N.Y.) and reverse-transcription polymerase chain reaction (RT-PCR) (Watson, J. D. et al. (1992) in "Recombinant DNA" Second Edition, W. H. Freeman and Company, New York). One preferred method is Northern blotting.

The nucleic acid sequence used as a probe for detecting VHL-specific mRNA expression is substantially homologous to SEQ. ID. NO. 1. By "substantially homologous" is meant a level of homology between the nucleic acid sequence and the cDNA sequence of SEQ ID NO.1. Preferably, the level of homology is in excess of 70% more preferably in excess on 80%, with a particularly preferred nucleic acid sequence being in excess of 90% homologous with the cDNA sequence shown in SEQ ID No. 1.

A most preferred method is reverse transcription-polymerase chain reaction (RT-PCR) where the primers used to amplify the cDNA produced via reverse transcription of RNA are derived from the cDNA sequence shown in SEQ ID No. 1. These primers can be labelled as described earlier and the RT-PCR products can be analyzed for mutations of the VHL gene associated with VHL disease via denaturing polyacrylamide gel electrophoresis of the RT-PCR products or via direct sequencing of the RT-PCR products.

The present invention also encompasses recombinant proteins derived from the cDNA shown in SEQ ID No. 1 and antibodies directed to said proteins (called VHL proteins). Recombinant VHL proteins can be produced by recombinant DNA methodology known to one skilled in the art. For example, a nucleic acid sequence capable of encoding a protein comprising all or part of the amino acid sequence shown in SEQ ID NO.2 can be cloned into a vector capable of being transferred into, and replicated in, a host organism. A suitable nucleic acid sequence for the purpose of this invention is the sequence shown in SEQ ID NO.1. Suitable expression vectors include, but are not limited to, vaccinia virus vectors include, baculovirus vectors, and *Ecoli* pTRCHIS (Invitrogen Co. San Diego). The recombinant expression vector produced by inserting a nucleic acid sequence capable of directing synthesis of VHL protein in a suitable expression vector can be transfected into *E coli* or into suitable eukaryotic cell systems by methods known to one skilled in the art.

Cells containing the expressed recombinant VHL protein, cell lysate from cells transfected with a recombinant expression vector or a culture supernatant containing the expressed VHL protein can be used as an immunogen to elicit production of anti-VHL antibodies in a mammal. Alternatively, one can generate synthetic peptides for use as immunogens from the amino acid sequence shown in SEQ ID NO 2. Preferred synthetic peptide sequences for use as an immunogen are shown below:

SEQ ID NO. 9:
Glu Glu Tyr Gly Pro Glu Glu Asp Gly Gly Glu Glu Ser Gly
SEQ ID NO. 10:
Gly Thr Gly Arg Arg Ile His Ser Tyr Arg Gly His Leu

While it is possible for the immunogen to be a administered to the mammal in pure or substantially pure form, it is preferable to present it as a pharmaceutical composition, formulation or preparation. Suitable mammals for immunization include mice, rabbits and the like. The anti-VHL antibody of the present invention is typically produced by immunizing a mammal with an immunologically effective amount of synthetic peptide of this invention. The preparation of polyclonal or monoclonal antibodies against such a peptide is well known in the art (Standt et al. (1988) J. Exp. Med. 157:687–704). The anti-VHL peptide antibody molecules induced by immunization of a mammal with the recombinant VHL protein are then collected from the mammal and those immunospecific for the VHL protein are isolated to the extent desired by well known techniques such as, for example, immunochromatography.

In a third embodiment, the method for detecting carriers of the VHL disease gene comprises analyzing the protein of a subject for alterations in VHL protein expression with VHL disease.

For analysis of protein by this method, protein is obtained from biological specimens such as tumor biopsy samples and urine and the like. The protein can be obtained as a crude lysate or it can be further purified by methods known to one skilled in the art (Sambrook, J. et al. (1989) in "Molecular Cloning, A Laboratory Manual", Cold Spring Harbor press, Plainview, N.Y.).

Crude protein lysate can be analyzed for VHL protein by immunoassays using anti-VHL antibody.

Immunoassays of the present invention may be a radioimmunoassay, Western blot assay, immunofluorescent assay, enzyme immunoassay, chemiluminescent assay, immunohistochemical assay and the like. Standard techniques known in the art for ELISA are described in *Method in Immunodiagnosis*, 2nd Edition, Rose and Bigazzi, eds., John Wiley and Sons, 1980 and Campbell et al., *Methods of Immunology*, W. A. Benjamin, Inc., 1964, both of which are incorporated herein by reference. Such assays may be a direct, indirect, competitive, or noncompetitive immunoassay as described in the art. (Oellerich, M. 1984. *J. Clin. Chem. Clin.* BioChem. 22:895–904).

Detection of the VHL protein anti-VHL antibody complex formed, can be accomplished by reaction of the complex with a secondary antibody such as labelled anti-rabbit antibody. The label may be an enzyme which is detected by incubating the complex in the presence of a suitable fluorimetric or calorimetric reagent. Other detectable labels may also be used, such as radiolabels, or colloidal gold, and the like. The labelled VHL protein-anti-VHL antibody complex is then visualized by autoradiography.

The present invention also relates to a method for treating a carrier of the VHL disease gene in which an expression vector containing a nucleic acid sequence representing the wild type VHL gene is administered to the carrier. A nucleic acid sequence representing wild-type VHL gene is that shown in SEQ ID No. 1. Such nucleic acid sequence may be inserted into a suitable expression vector by methods known to those skilled in the art (Example 5). Expression vectors suitable for producing high efficiency gene transfer in vivo include retroviral, adenoviral and vaccinia viral vectors.

Expression vectors containing a nucleic acid sequence representing wild-type VHL gene can be administered intravenously, intramuscularly, subcutaneously, intraperitoneally or orally. A preferred route of administration is intravenously.

The invention also provides a diagnostic kit for detecting carriers of the VHL disease gene. This diagnostic kit comprises purified and isolated nucleic acid sequences according to SEQ ID. No. 3 through SEQ ID No. 8, said sequences useful as PCR primers in analyzing DNA for mutations of the VHL disease gene linked to VHL disease.

Any articles or patents referenced herein are incorporated by reference. The following examples illustrate various aspects of the invention but are in no way intended to limit the scope thereof.

Materials

The subjects analyzed in the following examples were kindred identified by ophthalmologists, urologists, medical geneticists and neurosurgeons in the United States, Europe, and Canada. The members of the families resided in Louisiana, Tennessee, Mississippi, Virginia, Pennsylvania, New York, Michigan, Quebec, Nova Scotia, United Kingdom, and the Netherlands. Medical records of each family member known to be affected were reviewed. Asymptomatic family members and family members in whom there was uncertainty about the diagnosis were examined after informed consent for occult evidence of the illness at the Clinical Center of the National Institutes of Health. The examination consisted of a history and physical examination of the scrotum. An asymptomatic member of a VHL family was considered to be affected if one or more of the following disease manifestations were detected: retinal angioma(s), spinal or cerebellar hemangioblastoma(s), pheochromocytoma(s), multiple pancreatic systs, and multiple bilateral renal cysts accompanied by renal cell carcinoma. Disease diagnosis was made without knowledge of restriction fragment length polymorphism (RFLP) status.

Restriction enzymes were from Bethesda Research Laboratory (BRL) (Bethesda, Md.), New England Biolabs (Beverly, Mass.) and Boehringer Mannheim (Indianapolis, Ind.) and were used as recommended by the manufacturers. $\delta$-$^{32}$PdCTP (~3000 iu/mmol) was from Amersham (Arlington Heights, Ill.). The various human tissue polyadenylated RNAs used in Northern blotting were purchased from Clonstech (Palo Alto, Calif.) as was the adult kidney double-stranded complementary DNA sample. PCR and RT-PCR bits were from Perkin Elmer/Cetus (Norwalk, Conn.); deoxynucleotide triphosphates and fluorescently labelled dideoxynucleotides were from Applied Biosystems, Inc. (Foster City, Calif.). Nylon membranes were purchased from MSI, Inc. (Westlore, Mass.).

Methods

Southern and Northern blottings, filter hybridization and probe labelling were by random priming were performed by standard protocols (Sambrook, J. et al. (1989)). DNA inserts were purified following the GeneClean (Bio 101) (BioRad, Richmond, Calif.) protocol and used for subcloning or labelling. Oligonucleotides used as primers in PCR or RT-PCR or for sequencing were synthesized on the Applied Biosystems, Inc. Model 392 DNA/RNA synthesizer, according to the manufacturers recommendations. Pulse field goal electrophoresis was carried out using CHEF-DRII or CHEF mapper XA systems as described by the manufacturer (BioRad) under conditions optimal for obtaining the desired resolution.

The PCR was performed in a 50 ul reaction volume in a mixture containing 1 uM of each primer, 250 uM of each deoxynucleotide triphosphate, 5 ul of 10X PCR buffer (500 MM KCl; 120 MM Tris-HCl, pH 8.0; 1.5 MM $MgCl_2$; and 0.1% gelatin) and 1.25 units of AmpTaq (Cetus) DNA polymerase, in a first generation automated thermal cycler (Perkin-Elmer/Cetus). The PCR conditions consisted of 40 cycles of denaturation for one minute at 94° C., annealing for one minute at specified temperatures (55°–65° C.) and extension for 4 minutes at 72° C. followed by 7 minutes of final extension of 72° C.

RNA Preparation and Northern Blotting—Total cellular RNA was isolated by extraction of lymphoblastoid cell lines of affected VHL patients or kidney tissues in guanidine thiocyanate followed by centrifugation through a 5.7M CsCe cushion according to standard protocols (Sambrook, J. et al. (1989)). RNA samples were separated by electrophoresis in 1% agarose gels containing 2.2M formaldehyde, transferred to nylon membranes and hybridized to g7 cDNA probe (Sambrook, J. et al. (1989)).

RT-PCR—About 5 ug of total cellular RNA was isolated by extraction of lymphoblastoid cell lines or kidney tissues of VHL patients or 2.5 ng of normal adult kidney double-stranded complementary DNA samples were analyzed for expression using RT-PCR kit from Perkin-Elmer/Cetus. The primers were derived from the g7 cDNA sequence shown in SEQ ID NO. 1 and the reactions were run using various annealing temperatures. The reaction products were analyzed by gel electrophoresis and Southern blotting (Sambrook, J. et al (1989)).

EXAMPLES

Example 1

Isolation of the VHL Disease Gene

Figure 1:
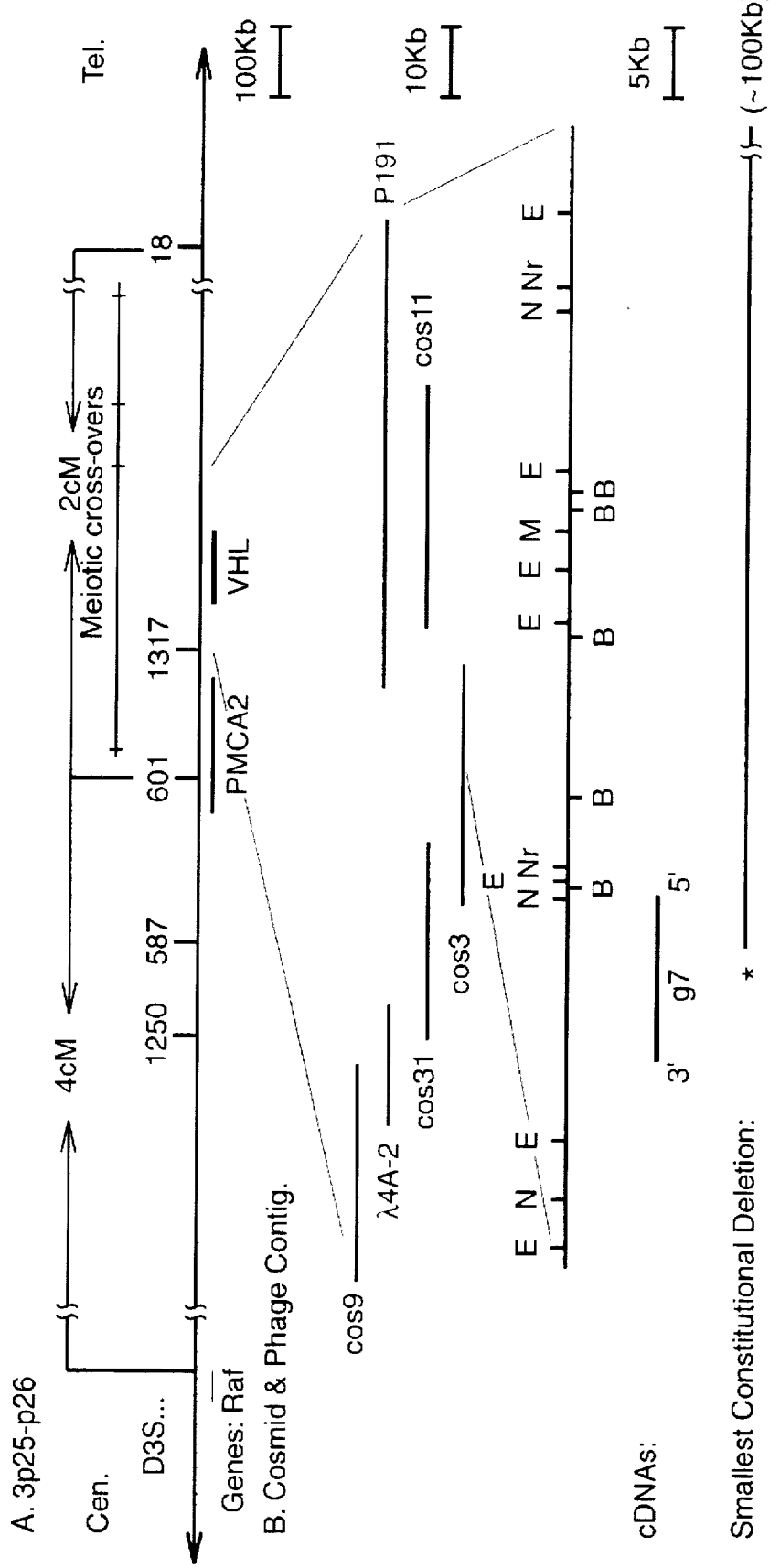
FIG. 1(A) shows a genetic and physical map of the chromosome 3p region encompassing the VHL gene. Genetic and physical distances between selected markers are shown in centiMorgans and kilobases respectively. The location of selected cross-overs is indicated by crosses.
FIG. 1B shows the 160 kb cosmid and phage contig covering the VHL region. An enlarged restriction map of cos3, cos11, and phage p191 detailing the position of g7 cDNA isolated by screening a λgt11 teratocarcinoma cDNA library with a conserved 7 kb fragment from the centromeric end of cos11. The beginning of the smallest constitutional deletion is indicated by an asterisk and line. Restriction sites: B, Bam HI; E, Eco RI; N, Not I; Nr, Nru I; M, Mlu I.

The isolation of the VHL disease gene resulted from the use of positional cloning strategies (Latif et al., Cancer Res. (1993) 63:861–867; Trofatter et al., Cell (1993) 72:791–800 and The Huntington's Disease Collaborative Research Group; Cell (1993) 72:971–983) previously used in isolating disease genes and is described in Latif et al. (Science, in press, "Identification of the von Hippel-Lindau Disease Tumor Suppressor Gene"). Genetic and physical map of the chromosome 3p region encompassing the VHL gene is shown in FIG. 1. The VHL locus was positioned on the map (FIG. 1A) by multipoint linkage analysis and meiotic mapping (Tory et al., 1989); the location of selected cross-overs is indicated by crosses.

YAC Library Screening and Analysis of YACS. Copies of the WU and CEPH YAC libraries were obtained from Dr. Craig Chinault (Baylor Institute of Human Genetics, Houston, Tex.) and Dr. Daniel Cohen, respectively (centre d' Etude du Polymorphisme Humain, Paris). The WU and CEPH libraries are total human genomic DNA libraries constructed in the PYAC4 vector (Burke, D. T. et al. Science (1987) 236:806–812; Anand, R. et al. Nucleic Acids Res. (1990) 18:1951–1956). These libraries were screened by sib selection using PCR-based techniques (Greene, E. D. et al., Proc. Natl. Acad Sci. (1990) 87:1213–1217) with primers for the D3S601, D3S587 and D3S18 loci in the VHL region (FIG. 1). The sequences of the primers used to positively identify YACs Y52A10, YA101D4, Y132F2 and Y70D2 are shown below as SEQ ID No. 11 thru SEQ ID No. 16:

| Locus/ Location | Designation | Sequence |
|---|---|---|
| D3S18/ 3p26 | ML-1 | CACAAGTGAT GCCTTGTAGC TG No. 11 |
| D3S18/ 3p26 | ML-2 | CAGTAGTGTC CTGTATTTAG TG No. 12 |
| D3S601/ 3p25.3 | ML-7 | GTTGGCTATG GGTAGAATTG G No. 13 |
| D3S601/ 3p25.3 | ML-8 | CAGGGTAGCC TTGATCTAAG T No. 14 |
| D3S587/ 3p25.2 | ML-10 | GGAGGTCCTG AGAATATGTG TCC No. 15 |
| D3S587/ 3p25.2 | ML-11 | TGTTCAGGCA CACAGTAGAT G No. 16 |

Screening Chromosome 3 Cosmid Library and Cosmid Contig Assembly. The chromosome 3 cosmid library was constructed as described in Lerman et al. (Lerman, M. I. et al. Hum. Genet. (1991) 86:567–577). This library was screened by colony hybridization (Sambrook, J. et al. (1989)) using the YAC DNA inserts as probes as described in Baxendale et al. (Baxendale, S. et al. Nucl. Acids Res. (1991) 19:6651). After labeling with $^{32}$P-dCTP, the probes were preassociated with a 1000X excess of sheared human DNA. Cosmid contigs were constructed by finding overlapping bands on Southern blots of EcoRI-digested cosmids using whole cosmids as probes. Gaps in the cosmid contigs were closed by chromosome walking using insert-end fragment probes, which were identified by restriction mapping and hybridization to restricted genomic DNA. These insert-end fragment probes were used for each walk step. FIG. 1(c) shows the 160 kb cosmid and phage contig covering the VHL region. The phage T42 was isolated by screening a total genomic phage library with YAC DNA inserts as described above. The phage p191, which contains the VHL disease gene, was isolated by screening a three-hit P1 phage genomic library (Genome System, Inc. St. Louis, Mo.) with primers chosen from within an exon of the g7 cDNA sequence shown in SEQ ID NO. 1. The phage p191 was deposited with the ATCC on May 13, 1993 and has been granted ATCC Deposit No. 69311.

Example 2

Isolation of a cDNA Corresponding to VHL Disease Gene

Screening cDNA Libraries. A λgt11 teratocarcinoma library (gift of Dr. Maxine Singer, National Cancer Institute) was screened by plaque hybridization (Sambrook, J. et al. (1989)) to 10° filter-immobilized cDNA phage clones at a density of 4×10$^4$ pfu/150-mm filter. FIG. 1B shows the position of the g7 cDNA isolated by screening the λgt11 teratocarcinoma cDNA library with a conserved 7 kb fragment at the centromeric end of cos11 used as a probe in the screening. The orientation of the g7 cDNA was established by sequencing and restriction mapping to the contig. The beginning of the smallest constitutional deletion is indicated by an asterisk and line. Restriction sites: B, Bam HI; E, Eco RI; N, Not I; Nr, Nru I; M, Mlu I.

cDNA Sequence and Sequence Analysis. The g7 cDNA clone was sub-cloned into the Bluescript KS (+) plasmid (Stratagene, La Jolla, Calif.). Double-stranded plasmid DNA was used in sequencing reactions performed with Taq Dye Deoxy terminator cycle sequencing kits (Applied Biosystems, Inc.). All sequences were obtained by running the reactions in an ABI 373A automatic sequencing system (Applied Biosystems, Inc.). Initial sequencing was performed with T3 and T7 primers, and "walking" primers were then constructed to continue sequencing. The cDNA clone was sequenced multiple times in one orientation or both orientations. Database searching, sequence editing, sequence assembly, and sequence analysis were carried out with the University of Wisconsin Genetics Computer Group sequence analysis software package, version 7.0 (Devereaux, J. et al. Nucl. Acids Rev. (1984) 12:387–395). The sequence of the g7 cDNA is shown in SEQ ID No. 1. This cDNA was deposited with the ATCC on May 13, 1993 and has been granted ATCC Deposit No. 69312. The cDNA sequence revealed an open reading frame (ORF) of 284 amino acids indicating that the rest represents part of the 3' untranslated region of the mRNA. This ORF showed a high probability score (>95%) for being a protein coding sequence Fickett, J. W., Nucl. Acids Rev. (1982) 10:5303). Neither the nucleotide nor the predicted amino acid sequences showed any significant homology to genes or proteins in the databases.

Example 3

Detection of q7-Specific mRNA Expression in Target Tissues

RNA Preparation and Northern Blotting Analysis. To identify the VHL gene, we evaluated the g7 loci was evaluated by analyzing its expression in target tissues.

Figure 2A:
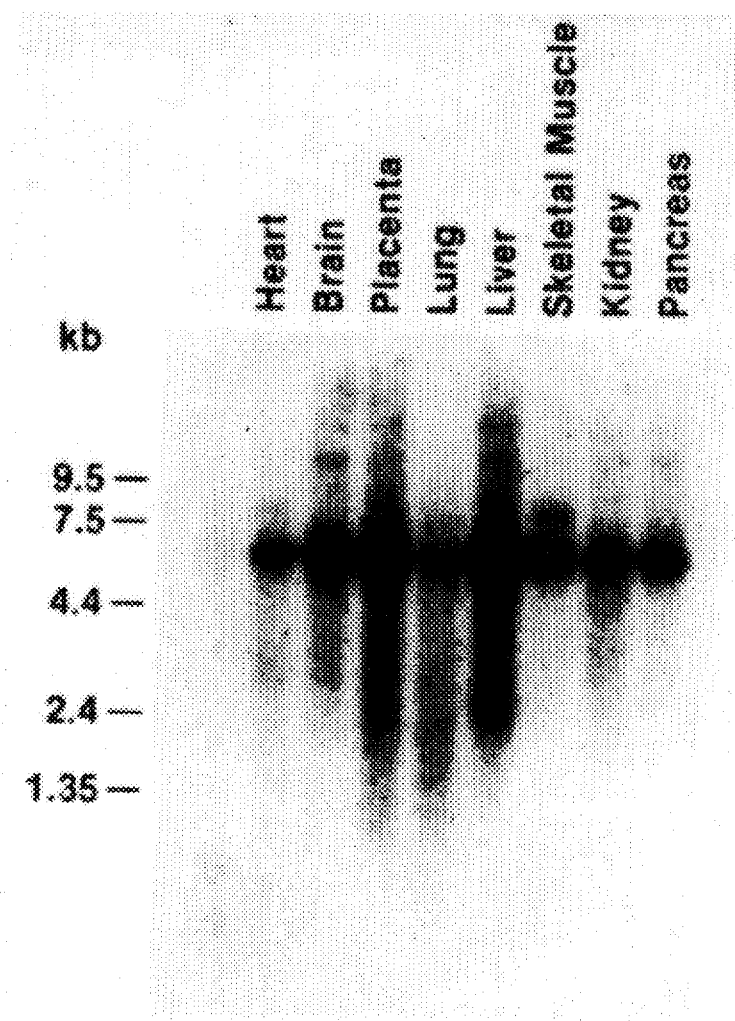
FIGS. 2A–B show Northern blot analysis of the expression of the gene represented by g7 cDNA in various human tissues.
Figure 2B:
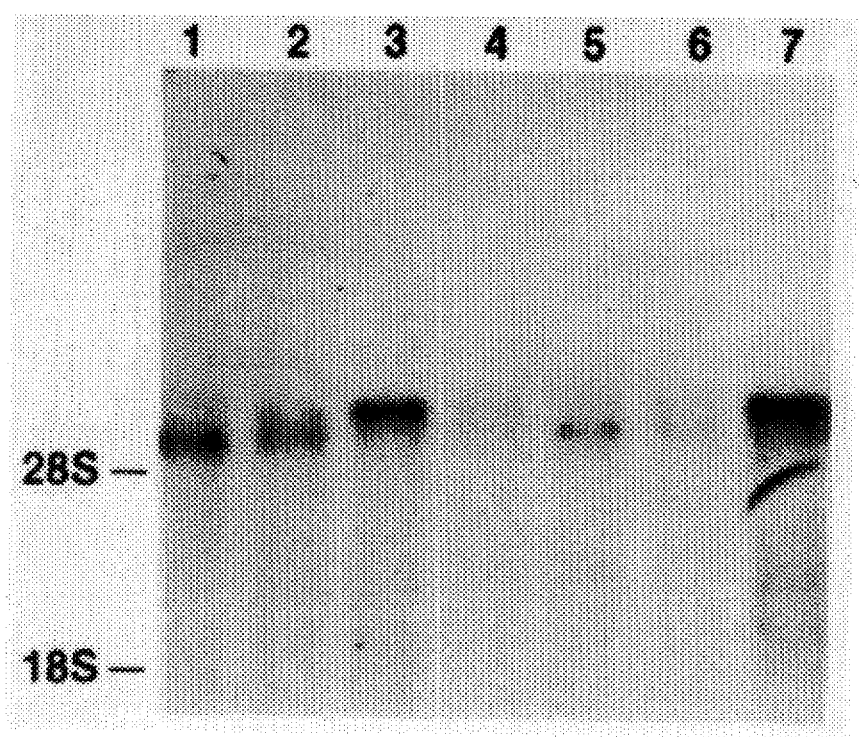

The expression pattern of the g7 gene was examined by Northern (RNA) blotting. FIG. 2A shows a low resolution blot where each lane contains poly A$^+$ mRNA (2 µg) from: lane 1, fetal brain; lane 2, adult brain; lane 3, fetal kidney; lane 4, adult kidney; lane 5, adult cerebellum; lane 6, adult adrenal; and lane 7, adult prostate while FIG. 2B shows a high resolution blot of 1 ug of poly A$^+$ mRNA from tissues as indicated in FIG. 2A. The sizes of the transcripts were determined from the position of the 28S and 18S rRNA bands of total RNA run on the same gel. Transcripts were observed in all human tissues tested, including brain and kidney, tissues frequently affected in VHL disease. The transcripts were of two distinct sizes, 6 and 6.5 kb, and were expressed in a tissue-specific and developmentally selective manner, i.e. only 6 kb or the 6.5 kb species was expressed in fetal brain and fetal kidney, while both were expressed in adult tissues. The two transcripts may represent alternatively spliced forms of g7 mRNA.

Example 4

Detection of Mutations of the VHL Disease Gene Associated With VHL Disease

RT-PCR Studies of Gene Expression. In order to detect mutations in constitutional DNA of affected patients in pedigrees and in new mutation patients, was conducted an extensive search for mutations (i.e. small intragenic and nonoverlapping deletions or insertions) which were of the loss -of- function type was conducted in constitutional DNA derived from 221 unrelated VHL patients. Southern blot analysis of genomic DNA isolated from the blood (Sambrook, J. et al. (1989)) of seven patients and then digested with EcoRI is shown in FIG. 3A. This blot was probed using the g7 cDNA as probe and this probe has been shown to detect a single invariant 20–22 kb EcoRI fragment in normal DNA, as determined by previous tests on more than 100 unrelated DNA samples provided by Centre d'Etude du Polymorphisme Humain (CEPH). A high incidence (>12%) of aberrant bands was observed with the bands ranging in size from 4 to 25 kb (FIG. 3A) and thus classified these VHL patients were thus classified as new mutations.

Example 5

Detection and Mapping of Deletions of the VHL Disease Gene

Figure 4:
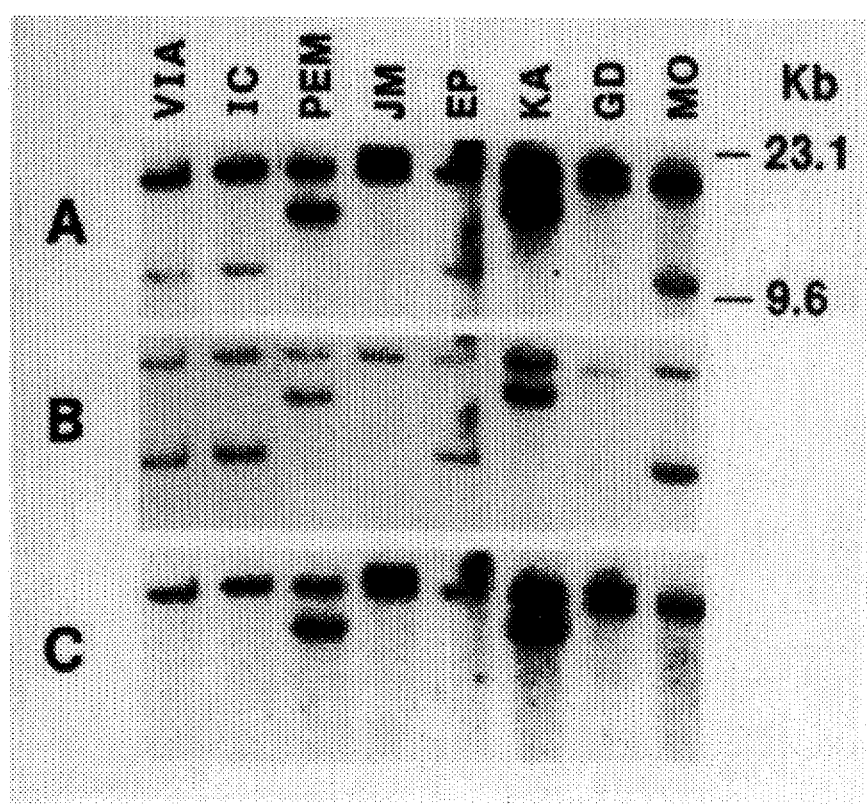

To prove the presence of deletions and to map them precisely, subfragments representing region of the g7 cDNA generated by PCR used as probes in Southern blotting analysis of genomic DNA isolated from blood of VHL patients and digested with EcoRI. (FIG. 4, where the probes used in each panel are: FIG. 4A, total g7 cDNA; FIG. 4B, nucleotides 3–146 of g7 cDNA; and FIG. 4C, nucleotides 1277–1600 of g7 cDNA). The results unequivocally demonstrated that 18 of the rearrangements were deletions as only part of the cDNA failed to detect the novel band in each patient (FIG. 4).

These deletions could then be classified into three groups as shown in Table 1.

TABLE 1

Deletion analysis of VHL patients with aberrant bands at the VHL locus (detected by g7 cDNA).

| Patient Code | Probe: cDNA 5'–>3' residue (s) | | | | | | Aberrant Band (kb) | Apparent Deletion Size (kb) |
|---|---|---|---|---|---|---|---|---|
| | 3–146 | 169–391 | 291–501 | 585–940 | 921–1231 | 1277–1600 | | |
| 3567 | ND | ND | ND | ND | ND | ND | 14 | ? |
| 3607 | ND | ND | ND | ND | ND | ND | 12 | ? |
| 3639 | ND | ND | ND | ND | ND | ND | 14 | ? |
| 3648 | ND | ND | ND | ND | ND | ND | 13 | ? |
| 3654 | ND | ND | ND | ND | ND | ND | 14 | ? |
| JD | ND | ND | ND | ND | ND | ND | 17 | ? |
| PEM | ND | ND | ND | ND | ND | ND | 15 | ? |
| MS | ND | ND | ND | ND | ND | ND | 15 | ? |
| KA | ND | ND | ND | ND | ND | ND | 15 | ? |
| 3547 | D | D | D | ND | ND | ND | 23–25 | 15–18 |
| JM | D | D | D | ND | ND | ND | 23–25 | 15–18 |
| GD | D | D | D | ND | ND | ND | 23–25 | 15–18 |
| 3512 | ND | ND | ND | ND | D | D | 10 | 11 |
| 3516 | ND | ND | ND | ND | D | D | 10 | 11 |
| 3557 | ND | ND | ND | ND | D | D | 10 | 11 |
| 3574 | ND | ND | ND | ND | D | D | 10 | 11 |
| VIA | ND | ND | ND | ND | D | D | 10 | 11 |
| IC | ND | ND | ND | ND | D | D | 10 | 11 |
| NE | ND | ND | ND | ND | D | D | 10 | 11 |
| EP | ND | ND | ND | ND | D | D | 10 | 11 |
| MO | ND | ND | ND | ND | D | D | 10 | 11 |
| 3569 | ND | ND | ND | D | D | D | 12 | 9 |
| 3667 | ND | ND | ND | D | D | D | 10 | 11 |
| 3761 | ND | ND | ND | D | D | D | 4 | 17 |
| 3819 | ND | ND | ND | D | D | D | 12 | 9 |

ND = Not deleted
D = Deleted

In order to determine that the single aberrant bands originating from the 20–22 kb invariant fragment were deletions or insertions within this fragment or deletions removing the flanking Eco RI sites, Southern blot analysis was conducted with several other restriction enzyme digests besides Eco RI (Bam HI, Bgl I, Bgl II, Dra I, Eco RV, Hind III, Pst I, and Pvu II). The results of the Southern analysis with a few of these enzymes is shown in FIG. 3B. These results demonstrated that the mutations were transmitted with the disease. FIG. 3c shows the results of Southern blotting analysis of DNA isolated form a regular VHL family (coded "P" ) and digested with EcoRI. The results clearly demonstrate transmission of the mutant allele (the aberrant band) in this VHL family.

The finding of three overlapping deletions within the same cDNA provides strong evidence for the identification of the g7 cDNA as the VHL gene.

Example 6

Detection of Intragenic Deletions or Insertions by PCR-SSCP and RT-PCR

To find intragenic deletions or insertions, genomic DNA isolated from VHL patient lymphoblastoid cell lines (Lymphoblastoid cells were immortalized by transformation with Epstein Barr Virus according to standard protocols (Nilison, K. et al., Adv. Cancer Res. (1982) 37:319–380)) was analyzed for alterations by PCR-single-strand-conformational polymorphism (PCR-SSCP) analysis using primers shown in SEQ ID NO. 3 thru SEQ ID NO. 8 and RNA isolated from sporadic renal cell carcinoma (RCC) cell lines (Anglard, P. et al. Cancer Res. (1992) 52:348–356) was analyzed by reverse transcription-polymerase chain reaction (RT-PCR). The primers used for RT-PCR of the RCC cell lines are shown as SEQ ID NO. 17 thru SEQ ID NO. 20:

SEQ ID NO. 17
CATCTTCTGC AATCGCAGTC CGCGCGT
SEQ ID NO. 18
CAAAAGCTGA GATGAAACAG TGTAAGT
SEQ ID NO. 19
GTTTGGTTAA CCAGAAGCCC ATCGT
SEQ ID NO. 20
GATGGGCTTC TGGTTAACCA AACT whose SEQ ID NO. 17 and NO. 18 are on pair of primers and SEQ ID NO. 19 and SEQ ID NO. 20 are a second pair. The results of these analyses are shown in Table 2.

TABLE 2

Germ-line (VHL) and somatic (sporadic RCC) mutations in the VHL candidate gene.

| Patients | Mutation | Consequence |
| --- | --- | --- |
| VHL family | | |
| "VA" | 8 bp (TTGTCCGT) insertion after NT714 | frameshift |
| "E" | 9 bp in-frame deletion (NT456–464) | Three amino acid (153–154) deletion (Arg Val Val) |
| "CS" | 3 bp in-frame deletion (NT434–436) | One amino acid deletion (146, Ile) |
| Sporadic RCC | | |
| "UOK118" | 1 bp deletion (NT737) | frameshift |
| "UMRC5" | 1 bp deletion (NT737) | frameshift |
| "UMRC6" | 10 bp deletion (NT715–724) | frameshift |
| "A498" | 5 bp deletion (NT638–642) | frameshift |
| "UOK151" | nonsense C → A (NT761) transversion | stop codon |

NT = (nucleotide(s)).

RCC were chosen because according to Knudson's dictum (Knudson (1971)) sporadic cancers should be associated with mutations in the same loci affected in the hereditary form of the same malignancy. So far aberrant patterns have been identified in five RCC cell lines and proved four of them have been proven to be small (1 to 10 bp) deletions creating frameshift mutations and truncated proteins (TABLE 2). The cell lines UMRC5 and RCC "UOK118" have the same 1 bp deletion at nucleotide 737, amino acid 246, creating 28 new amino acids followed by a stop codon. Incidentally, this deletion creates a new Eco RI site, leading to two aberrant bands on Southern blots (not shown). Line UMRC6 has a 10 bp deletion (nucleotides 715 to 724) creating a frameshift such that 32 new amino acids are present followed by a new stop codon. Finally, line A498 has a 5 bp deletion (nucleotides 638 to 642) leading to a premature stop after new 62 amino acids. In the fifth RCC cell line, UOK151, the change is a nonsense (stop codon) mutation resulting from a C to A transversion at nucleotide 761 (TCG→TAG), creating a truncated protein. These data suggest that the VHL disease gene plays an important role in sporadic kidney cancer. As such, RT-PCR or PCR-SSCP as described in this application can be used as diagnostic methods to distinguish primary kidney tumors from tumors that spread to the kidney from other tissues or organs and to distinguish different histological types of kidney tumors.

In the DNA of the VHL lymphoblastoid cell lines derived from VHL patients, SSCP aberrant patterns segregating with the disease were also detected using primers shown in SEQ ID NO. 3 thru SEQ ID NO. 8. One (patient "VA") was found to be an 8 bp (TTGTCCGT) insertion after nucleotide 714. This insertion created a shift in the reading frame and a truncated protein. The second patient ("CS") had an in-frame 3 bp deletions leading to the removal of amino acid 146 (isoleucine).

Finally, patient "E" had an in-frame 9 bp deletion (nucleotides 456 to 464) that resulted in the removal of three amino acids (Arg Val Val) at position 153–155. These combined results strongly support the conclusion that the g7 gene represents the VHL and the sporodic RCC tumor suppressor gene.

Example 7

Conservation of the g7 cDNA Across Species

In order to determine whether the g7 cDNA is highly conserved across species ranging from mammals to Drosophila and sea urchin. Zoo blotting using g7 cDNA as a probe was performed on DNA isolated from human (*Homo sapiens*), chimpanzee (*Pan troglodytes*), macaque (*Macaca fascicularis*), cow (*Bovis domesticus*), rat (*Rattus norvigicus*), mouse (*Mus musculus*), chicken (*Gallus domesticus*), frog (*Xenopus laevis*), fly (*Drosophila melanogaster*), sea urchin (*Strongilocetrotus purpuratus*), and yeast (*Saccharomyces ceriviseae*), all purchased from BIOS Laboratories (New Haven, Conn., USA). (Pre) Hybridization was done in Church buffer [G. M. Church and W. Gilbert, Proc. Natl. Acad. Sci. U.S.A., 81, 1991 (1984)] at 65° C. for 18 hours. Blots were washed in 0.1× Church buffer at 60° C. for 60 min. The results of the zoo blot are shown in FIG. 6. The results demonstrate an extensive evolutionary conservation which is indicative of g7 serving a basic life function and also, of g7 having a tumor suppressor role.

The contents of all citations, i.e., journal articles, patents and the like, are incorporated herein by reference.

It is understood that the examples and embodiments described herein are for illustrative purposes and that various modifications and changes in light thereof to persons skilled in the art are included within the spirit and purview of this application and scope of the appended claims.

What is claimed is:

1. An antibody immunospecific for the protein product of the Von Hippel-Lindau disease gene.

2. The antibody of claim 1, wherein said antibody is selected from the group consisting of polyclonal and monoclonal antibodies.

3. A recombinant protein encoded by a purified and isolated Von Hippel-Lindau disease gene.

4. The recombinant protein of claim 3, wherein the recombinant protein is encoded by a purified and isolated Von Hippel-Lindau disease gene comprising SEQ ID NO: 1.

5. A method for detecting Von Hippel-Lindau protein in a biological sample comprising:

(a) contacting the biological sample with antibody having specific binding affinity for Von Hippel-Lindau protein to form an immune complex with said protein; and (b) detecting the presence of the immune complex.

6. The method of claim 5 wherein said step of contacting comprises Western blotting.

7. The method of claim 5, wherein said step of contacting comprises immunohistochemistry.

* * * * *